US006983182B2

(12) United States Patent
Mistretta

(10) Patent No.: US 6,983,182 B2
(45) Date of Patent: Jan. 3, 2006

(54) TIME RESOLVED COMPUTED TOMOGRAPHY ANGIOGRAPHY

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 497 days.

(21) Appl. No.: 10/219,457

(22) Filed: Aug. 20, 2002

(65) Prior Publication Data

US 2003/0013953 A1    Jan. 16, 2003

Related U.S. Application Data

(63) Continuation-in-part of application No. 09/767,757, filed on Jan. 23, 2001, now Pat. No. 6,487,435, which is a continuation-in-part of application No. 09/600,433, filed as application No. PCT/US98/26523 on Dec. 11, 1998, now Pat. No. 6,630,828, and a continuation-in-part of application No. PCT/US01/08477, filed on Mar. 16, 2001, which is a continuation-in-part of application No. 09/314,227, filed on May 18, 1999, now Pat. No. 6,381,486.

(60) Provisional application No. 60/348,110, filed on Nov. 9, 2001, provisional application No. 60/193,088, filed on Mar. 30, 2000, provisional application No. 60/115,259, filed on Jan. 8, 1999, provisional application No. 60/081,409, filed on Apr. 10, 1998.

(51) Int. Cl.
    *A61B 5/05*    (2006.01)

(52) U.S. Cl. ........................ 600/425; 382/131; 382/280
(58) Field of Classification Search ............ 378/21–27; 600/425–429; 382/131, 280, 284
See application file for complete search history.

(56) References Cited

U.S. PATENT DOCUMENTS

| 4,767,991 A | * | 8/1988 | Rzedzian ................... 324/312 |
| 5,602,891 A | | 2/1997 | Pearlman |
| 5,850,486 A | * | 12/1998 | Maas et al. ................. 382/294 |
| 6,018,600 A | * | 1/2000 | Levin et al. ................ 382/284 |
| 6,151,378 A | * | 11/2000 | Rasche et al. ................. 378/4 |
| 6,434,413 B1 | * | 8/2002 | Liu et al. .................... 600/410 |
| 6,487,435 B2 | * | 11/2002 | Mistretta et al. ............ 600/420 |
| 6,748,098 B1 | * | 6/2004 | Rosenfeld ................... 382/131 |

FOREIGN PATENT DOCUMENTS

WO    WO 98/01828    *    1/1998

* cited by examiner

*Primary Examiner*—Brian L. Casler
*Assistant Examiner*—Julianna M. Sullivan
(74) *Attorney, Agent, or Firm*—Quarles & Brady LLP

(57) ABSTRACT

A contrast enhanced dynamic study of a subject is performed with a CT system. A series of undersampled image data sets are acquired during the study with successive data sets acquired at interleaved projection angles. More fully sampled image data sets are formed by transforming the x-ray attenuation projection data to k-space and then sharing peripheral k-space data between undersampled k-space data sets. Artifacts due to undersampling are thus reduced without significantly affecting the time resolution of a series of reconstructed images.

21 Claims, 4 Drawing Sheets

TIME RESOLVED COMPUTED TOMOGRAPHY ANGIOGRAPHY

CROSS-REFERENCE TO RELATED APPLICATIONS

This application claims the benefit of U.S. Provisional Patent Application No. 60/348,110 filed Nov. 9, 2001 and is a continuation-in-part of U.S. patent application Ser. No. 09/767,757 filed on Jan. 23, 2001, now U.S. Pat. No. 6,487,435, which is a continuation-in-part of U.S. patent application Ser. No. 09/600,433 filed on Jan. 10, 2001, now U.S. Pat. No. 6,630,828, which is the national phase of PCT Application No. US98/26523 filed on Dec. 11, 1998, which has the benefit of earlier filed U.S. Provisional Patent Application No. 60/081,409 filed on Apr. 10, 1998. This application is also a continuation-in-part of PCT Application No. US01/08477 filed on Mar. 16, 2001, which has the benefit of earlier field U.S. Provisional Patent Application No. 60/193,088 filed on Mar. 30, 2000, which in turn is a continuation-in-part of U.S. patent application Ser. No. 09/314,227 filed on May 18, 1999, now U.S. Pat. No. 6,381,486, which claims the benefit of U.S. Provisional Patent Application No. 60/115,259 filed Jan. 8, 1999.

STATEMENT REGARDING FEDERALLY SPONSORED RESEARCH

This invention was made with government support under Grant No. HL62425 awarded by the National Institute of Health. The United States Government has certain rights in this invention.

BACKGROUND OF THE INVENTION

The present invention relates to computed tomography, and more particularly, to a method and apparatus for producing time resolved angiograms using a computed tomography ("CT") system.

In a computed tomography system, an x-ray source projects a fan-shaped beam which is collimated to lie within an X-Y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile".

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

Angiography is a diagnostic modality concerned with diseases of the circulatory system. Many imaging modalities are now available for researching vascular structures, including ultrasound, computed tomography, and magnetic resonance imaging. One of the most popular imaging modalities for angiography is digital subtraction angiography (DSA). In DSA, a pre-injection image (or mask) is obtained, a contrast agent is injected, and a series of images are acquired as the contrast agent flows into the vascular structures. The mask image is subtracted from the contrast enhanced images to remove background tissues and provide high contrast in vascular structures.

Although a number of angiographic imaging modalities are available, all of these known methods suffer from one or more disadvantages including sensitivity to artifacts from patient motion, low signal to noise ratio, and the requirement for a significant load of contrast agent to be inserted in the patient. Furthermore, although DSA had been developed with the hope of using it to perform intravenous contrast imaging, which is less invasive and less uncomfortable for the patient than arterial injection, attempts to provide such a system have been generally unsuccessful.

In Computer Rotation Angiography (CRA), a computed rotational angiography system such as that described by Fahrig, Lownie and Holdsworth (*Use of a C-Arm system to generate True 3D Computed Tomography Rotational Angiograms; Preliminary in vitro and In vivo Results*. R. Fahrig, S. Lownie, and D W Holdsworth, AJNR 18:1507–154, September 1997) is employed to acquire a series of three dimensional images during the uptake of a contrast agent. Because it is desirable to acquire the three-dimensional data sets obtained using this apparatus, as quickly as possible in order to provide a high time resolution during the dynamic study, only 120 projection angles, or views, are acquired. This is significantly less than that demanded by the Nyquist sampling theorem. Therefore, the angiogram reconstructed from a single data set contains streak artifacts. These streak artifacts preclude the use of this CRA method for intravenous angiography because of the reduced vasculature contrast provided by this contrast injection method.

SUMMARY OF THE INVENTION

The present invention is a method for producing time resolved angiograms following injection of a contrast agent using a high speed computed tomography system. The contrast agent can be injected through typical arterial injection, or intravenously, thereby reducing the invasiveness and discomfort of the procedure for the patient. The method of the present invention is used to acquire a time series of computed tomographic angiography (CTA) images rather than a single CTA image, thereby removing timing uncertainties found in typical CTA.

In the method of the present invention, a patient is placed in a CT system and an initial rotation is performed to acquire a pre-injection mask image. After the pre-injection mask is obtained, the contrast agent, is injected and then a series of undersampled images are acquired through successive rotations of the x-ray source and detector as the contrast agent flows into the vasculature being imaged. Each rotation of the gantry is performed at slightly different angular sampling orientations such that the projection angles of successively acquired undersampled images are interleaved with each other. Each projection is Fourier transformed to produce a corresponding set of k-space samples. Since the k-space data for successive undersampled images is interleaved, a fully sampled image can be formed by combining peripheral k-space data from temporally adjacent undersampled images without significant loss of time resolution. A series of fully sampled images may thus be reconstructed from the series of undersampled images.

An object of the invention is to provide high time resolution in a series of CTA images without producing streak artifacts. The rate at which projection data for each CTA image is acquired is increased by reducing the number of projection views during each revolution of the gantry. Streak artifacts which might otherwise occur due to undersampling are minimized by sharing interleaved data acquired for temporally adjacent CTA images.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENTS

Figure 1:
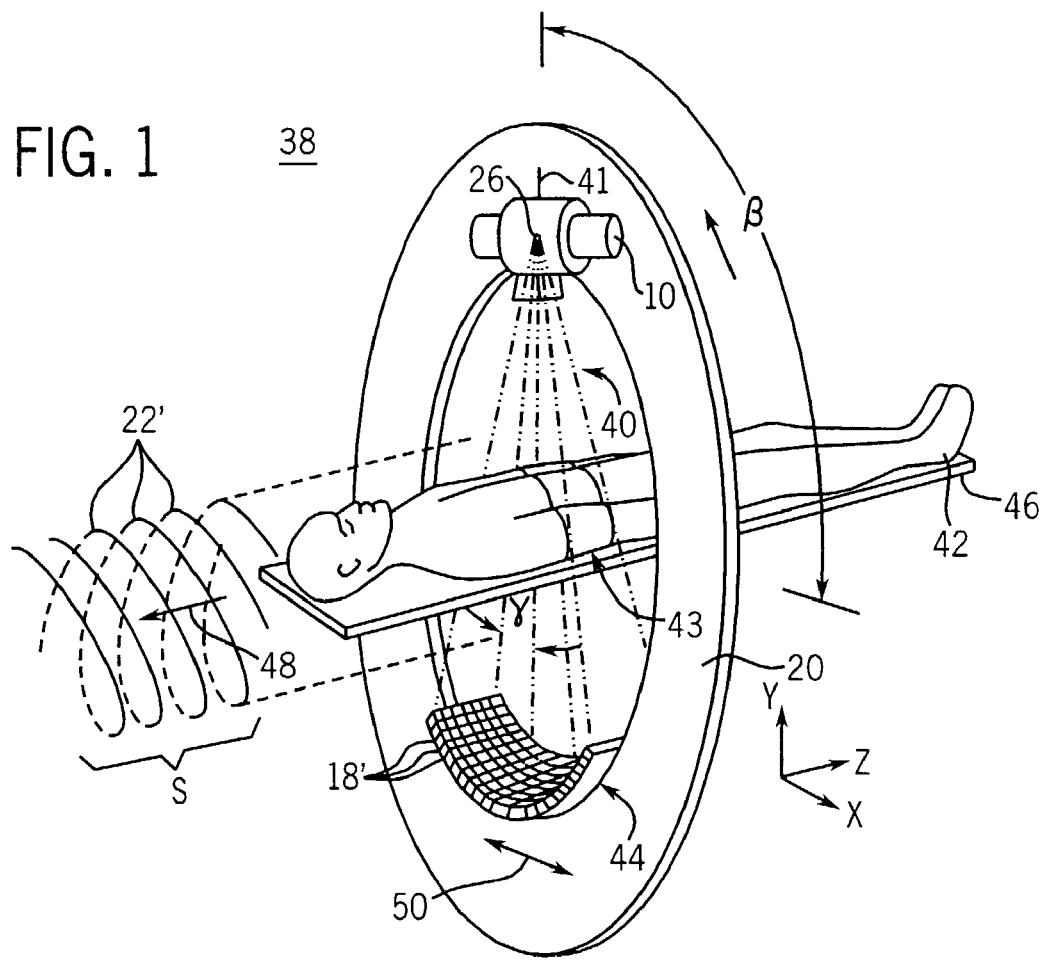
FIG. 1 is a perspective view of a first type of CT apparatus which can be used to practice the present invention which includes a detector array having rows and columns of detector elements and fan beam source.

Referring now to FIG. 1, a first embodiment CT scanner which employs the present invention includes a gantry 20 having an opening that defines an imaging area (not separately numbered) where gantry 20 supports an x-ray source 10 oriented to project a fan beam 40 of x-rays along a beam axis 41 through a patient 42 to an opposed two-dimensional detector array 44. The gantry 20 rotates to swing the beam axis 41 within a gantry plane 38 defining the x-y plane of a Cartesian coordinate system. Rotation of gantry 20 is measured by beam angle β from an arbitrary reference position within the gantry plane 38.

A patient 42 rests on a patient support table 46 which may be moved along a translation axis 48 aligned with a Z-axis of the Cartesian coordinate system. Table 46 passes through gantry plane 38 and is radio-translucent so as not to interfere with the imaging process.

The x-rays of the fan beam 40 diverge from the beam axis 41 within the gantry plane 38 across a transverse axis 50 generally orthogonal to both the beam axis 41 and the translation axis 48 at a fan beam angle γ. The x-rays of beam 40 also diverge from the beam axis 41 and the gantry plane 38 along the translation axis 48 (i.e., along the Z axis). After passing through patient 42, the x-rays of the fan beam 40 are received by two-dimensional detector array 44 which has detector elements 18' arranged in a plurality of rows, each extending along the traverse axis 50 and a plurality of columns, each extending along the translation axis 48. The surface of detector array 44 may be planar or may follow a section of a sphere or cylinder having a center at focal spot 26 at the system isocenter.

The detector elements 18' each receive x-rays and provide intensity measurements along separate rays of the fan beam 40. Each intensity measurement describes the attenuation via a line integral of one fan beam ray passing through a portion of a region of interest (ROI) 43 of patient 42. The ROI 43 is a three-dimensional volume in which a row of detector elements 18' measures beam attenuation at different locations in this volume along the transverse axis and a column measures beam attenuation at different locations along translation axis 48.

Figure 2:
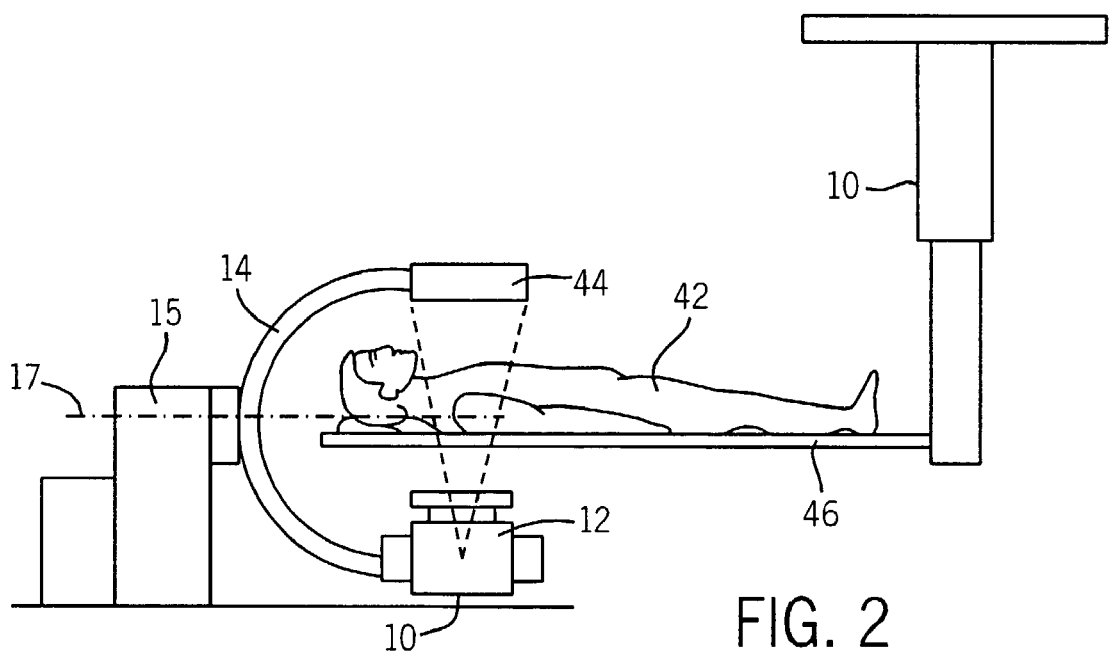
FIG. 2 is a perspective view of a second type of CT apparatus that can be used to practice the present invention wherein a C-arm is employed.

Referring now to FIG. 2, a second embodiment of a CT scanner which employs the present invention comprises a C-arm 14 to which the two-dimensional detector 44 and X-ray source 12 are mounted. Here, again the patient 42 is positioned on a table 46. The C-arm 14 is rotationally mounted to a base 15, and data for the generation of three-dimensional images is obtained by rotating the X-ray source 12 and detector 44 around a defined axis 17. CT scanners of the type shown in FIG. 2 are particularly useful in angiography, as described in *Use of a C-Arm system to generate True* 3D *Computed Tomography Rotational Angiograms: Preliminary in vitro and In vivo Results*. R. Fahrig, S. Lownie, and D W Holdsworth, AJNR 18:1507–154, September 1997.

Figure 3:
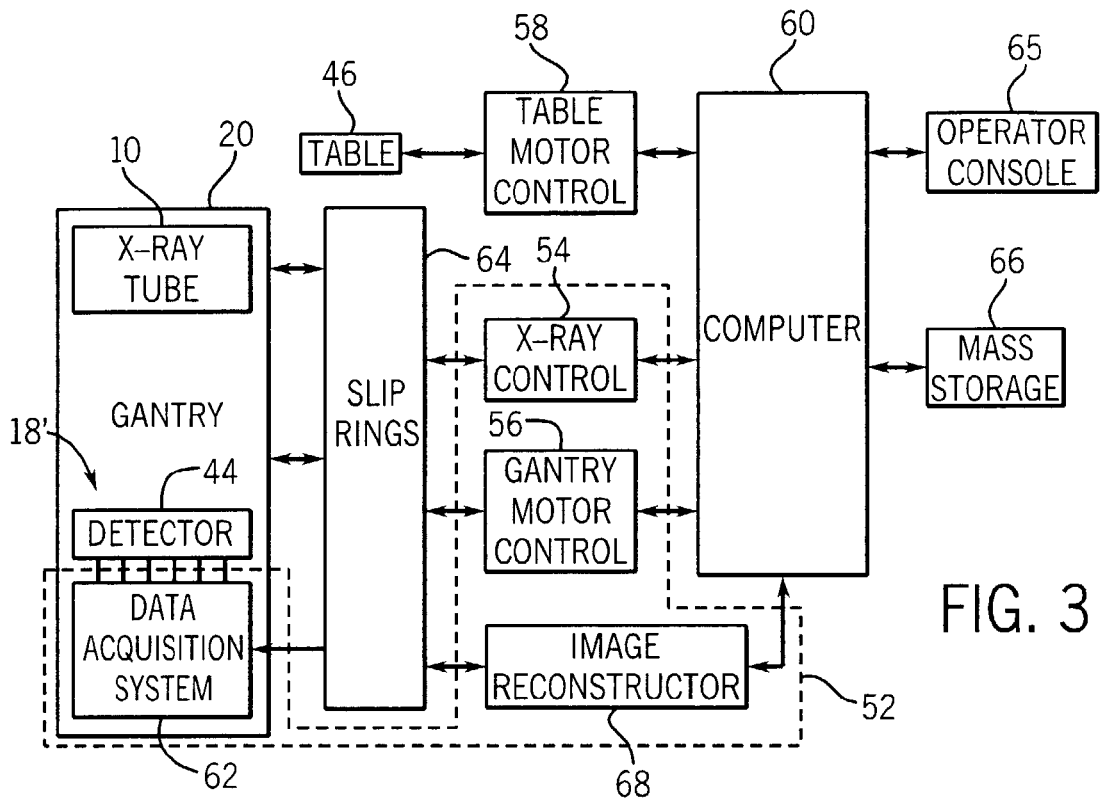
FIG. 3 is a block diagram of CT control system which can be used to control the CT apparatus of FIG. 1 and which is useful for the purposes of practicing the present invention.

Referring now to FIG. 3, an exemplary control system for controlling the CT imaging system of FIG. 1 or 2 includes a plurality of imaging control modules 52, a table motor control 58, a computer 60, an operator's console 65 and a mass storage device 66. The imaging control modules 52 include an x-ray control module 54, a motor control module 56, a data acquisition system 62 and an image reconstructor 68. The x-ray control 54 provides power and timing signals to the x-ray source 10 to turn the source on and off as required under the control of computer 60. The motor control 56 controls the rotational speed and position of the gantry 20 or C-arm 14 and provides positional information to computer 60. The table motor control 58 controls translation speed of table 46, if necessary, and provides position feedback information back to computer 60.

Data acquisition system 62 samples and digitizes intensity signals from the two-dimensional detector array 44 and provides the digitized signals to computer 60 which in turn stores the attenuation values in mass storage device 66. A slip ring connects all gantry mounted elements to other system components that are not mounted to the gantry for two way communication as is well known in the art. After data is collected, image reconstructor 52 is controlled to combine the collected data to form images, as described below. Reconstructed images can be displayed via console 65 or some other display device.

Referring to FIG. 3, computer 60 runs a pulse sequencing program to perform the angiography procedure described in more detail below. To this end, computer 60 receives commands and scanning parameters via operator console 65 which is generally a CRT display and keyboard. Console 65 allows an operator to enter parameters for controlling a data acquiring scan, to select images to be displayed and to display reconstructed images and other information from computer 60. The mass storage device or memory 66 provides a means for storing operating programs for the CT imaging system, as well as image data for future reference by the operator. Both computer 60 and image reconstructor 52 have associated electronic memory (not shown) for storing data.

In operation, motor control 56 controls the speed and direction of motion of the gantry 20 or C-arm 14. The table motor control 58 begins translation of the table 46. The x-ray control 54 turns on the x-ray source 10 and attenuation data is acquired on a continuous basis as imaging progresses through a defined imaging area. At each projection angle, a two-dimensional array of attenuation data is acquired from the columns and rows of array 44. As the gantry rotates, a succession of such two-dimensional arrays of data are acquired at a corresponding succession of view angles to produce a three-dimensional array of data. This 3D array of image data is stored in mass storage device 66 and can be weighted and filtered according to well-known methods.

In the present invention, scanners such as those described with reference to FIG. 1 and FIG. 2 above are employed to produce time resolved angiograms during a contrast enhanced dynamic study of the subject. Initial rotations are performed to acquire a pre-injection mask which can be used to remove the effects of bones and artifacts from successively acquired images. After the pre-injection mask data is obtained, a contrast agent, preferably iodine, is injected. The iodine can be injected through typical arterial injection, but is preferably introduced intravenously, thereby reducing the invasiveness and discomfort of the procedure for the patient.

Next, a time series of computed tomographic angiography (CTA) images are obtained to image the selected region of interest in the body. Rather than precisely timing the arrival of contrast into the vasculature being imaged, the strategy of a CTA dynamic study is to acquire a series of images during administration of the contrast agent. The physician is then able to select which image in the series best depicts the vasculature of interest. In addition to image quality and resolution, an important criteria in a CTA dynamic study is the rate at which images can be acquired. This is referred to as time resolution, and studies with higher time resolution increase the probability that an image with peak contrast in the vasculature of interest will be acquired.

In the preferred embodiment of the invention a series of 3D image data sets are acquired rapidly as the contrast agent arrives in the vasculature of interest. The temporal resolution is increased by reducing the number of projections acquired for each image. The full FOV image may be reconstructed without artifacts if the Nyquist condition is met. If this condition is not satisfied, however, alias-free reconstruction still occurs within a reduced diameter (d) that is less than the full FOV diameter (D). If it is assumed that the projections are acquired evenly spaced, then the surface area A at the periphery of k-space ($k_{max}$) associated with a projection is $$A = \Delta k^2 = \frac{2\pi}{N} k_{max}^2 \quad (1)$$

where N is the number of acquired views, or projections. Equation (1) determines Δk, by which the diameter (d) of the reduced FOV due to the angular spacing can be related to the full FOV diameter D as follows:

$$\frac{d}{D} = \frac{2}{N_R} \sqrt{\frac{N}{2\pi}}$$

where $N_R$ is the matrix size (i.e. number of attenuation samples in a projection) across the FOV. In the image domain, a well-constructed reduced FOV appears centered around each object even if the Nyquist condition is not met. However, radial streak artifacts from outside can enter the local FOV. The condition that k-space be fully sampled, or d=D, requires that the number of sampled projections be:

$$N = \frac{\pi}{2} N_R^2. \quad (2)$$

If $N_R$=512 samples are acquired along the transverse axis 50 during each CT system projection, for example, the number of projections N required to meet the Nyquist condition is around 800.

Figure 4:
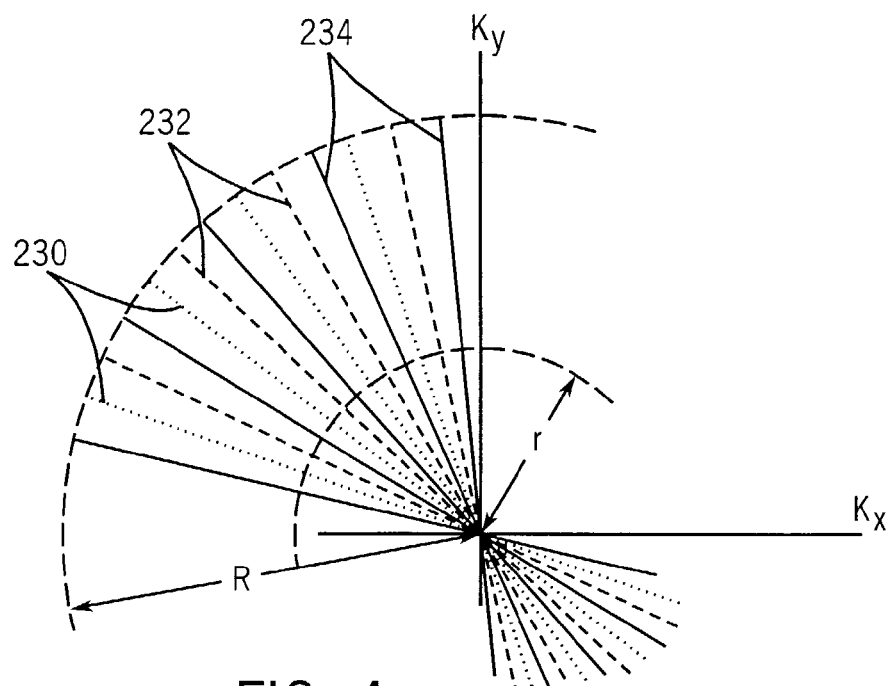
FIG. 4 is an illustration of the application of the present invention in a scanning procedure.

Referring to FIG. 4, if N projections are required to fully sample a k-space volume having a radius R, these N projections may be divided into three sets of interleaved projection views. The sampling trajectories of the first set of projection views are indicated by dotted lines 230, the second set is indicated by dashed lines 232, and the third set by lines 234. Because they are interleaved with the other sets and evenly spaced around the center of k-space, each set of projections 230, 232 and 234 acquire an image data set that is undersampled at its periphery, but is fully sampled at a smaller radius r. In other words, each set of projection views 230, 232 and 234 fully samples the center region of k-space, but undersamples the peripheral region of k-space.

Figure 5:
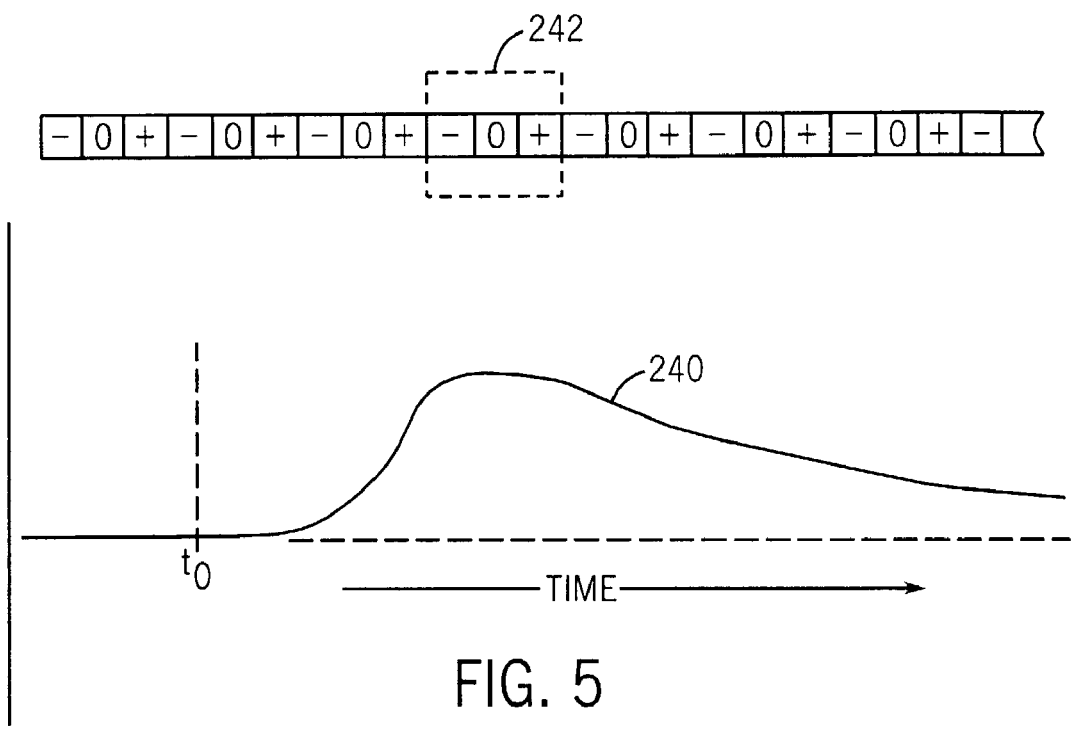
FIG. 5 is a graphic illustration of contrast enhancement during a dynamic study and the concurrent acquisition of image data with a CT system.

A CTA dynamic study is illustrated in FIG. 5, where the curve 240 indicates contrast enhancement in the vasculature of interest after a contrast agent is injected at time $t_0$. The image data is typically acquired beginning at a time prior to contrast arrival and lasting for a period of time well beyond the peak in signal contrast. The source and detector are rotated around the subject to acquire the first set of views 230 indicated by "0" in FIG. 5, rotated again to acquire the second set of views 232 indicated by "+" in FIG. 5 and then rotated again to acquire the third set of views 234 indicated by "−" in FIG. 5. This scan sequence is repeated throughout the dynamic study. It should be apparent that the time resolution of each view set 230, 232 and 234 is three times the time resolution of a complete, fully sampled acquisition comprised of all three view sets.

All of the data sets acquired during the dynamic study are stored. Typically, a mask image is produced by combining the samples from three view sets 230, 232 and 234 acquired prior to contrast arrival and reconstructing an image. The mask image may be subtracted from contrast enhanced images acquired as the contrast arrives to remove non-vascular structures as will be described in more detail below.

Figure 6:
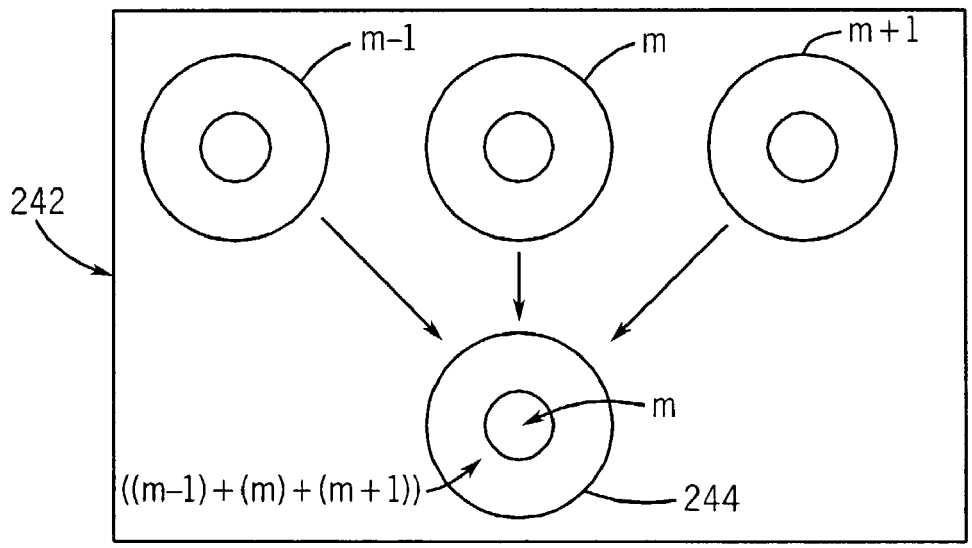
FIG. 6 is a pictorial representation of how k-space data for three successive undersampled images is combined to form a k-space data set for a fully sampled image.

Referring particularly to FIGS. 5 and 6, a contrast enhanced image may be produced by first sliding a data window 242 to any point (m) along the data sets acquired during the dynamic study. As shown in FIG. 5, the data window 242 may, for example, be aligned with the peak in arterial enhancement, although it can be appreciated that the window location m may be centered on any set of views acquired during the dynamic study.

An image is reconstructed by combining the data from the three undersampled sets of views 230, 232 and 234 within the data window 242. As will be described in more detail below, this is accomplished by Fourier transforming each acquired projection data set to produce corresponding k-space data sets and then using all of the k-space data in the center data set m and the peripheral k-space data from adjacent data sets m−1 and m+1. The central region of the view set m is fully sampled (i.e. out to radius r) and it accurately depicts the image enhancement occurring at its acquisition time during the study. The undersampled peripheral region surrounding the center (i.e. from the radius r to radius R) is filled in with peripheral data from the adjacent view sets at m−1 and m+1. As a result, a fully sampled image data set 244 is formed which depicts the vasculature of interest at time m during the dynamic study.

As indicated above, many different images can be produced from the data sets 230, 232 and 234 acquired throughout the dynamic study. A single image may be produced at a selected time m during the study as described above, or a series of images can be produced by sliding the data window 242 to successive data sets. The mask image may be subtracted and one or more 2D projection images may be produced from the resulting 3D difference image.

Figure 7:
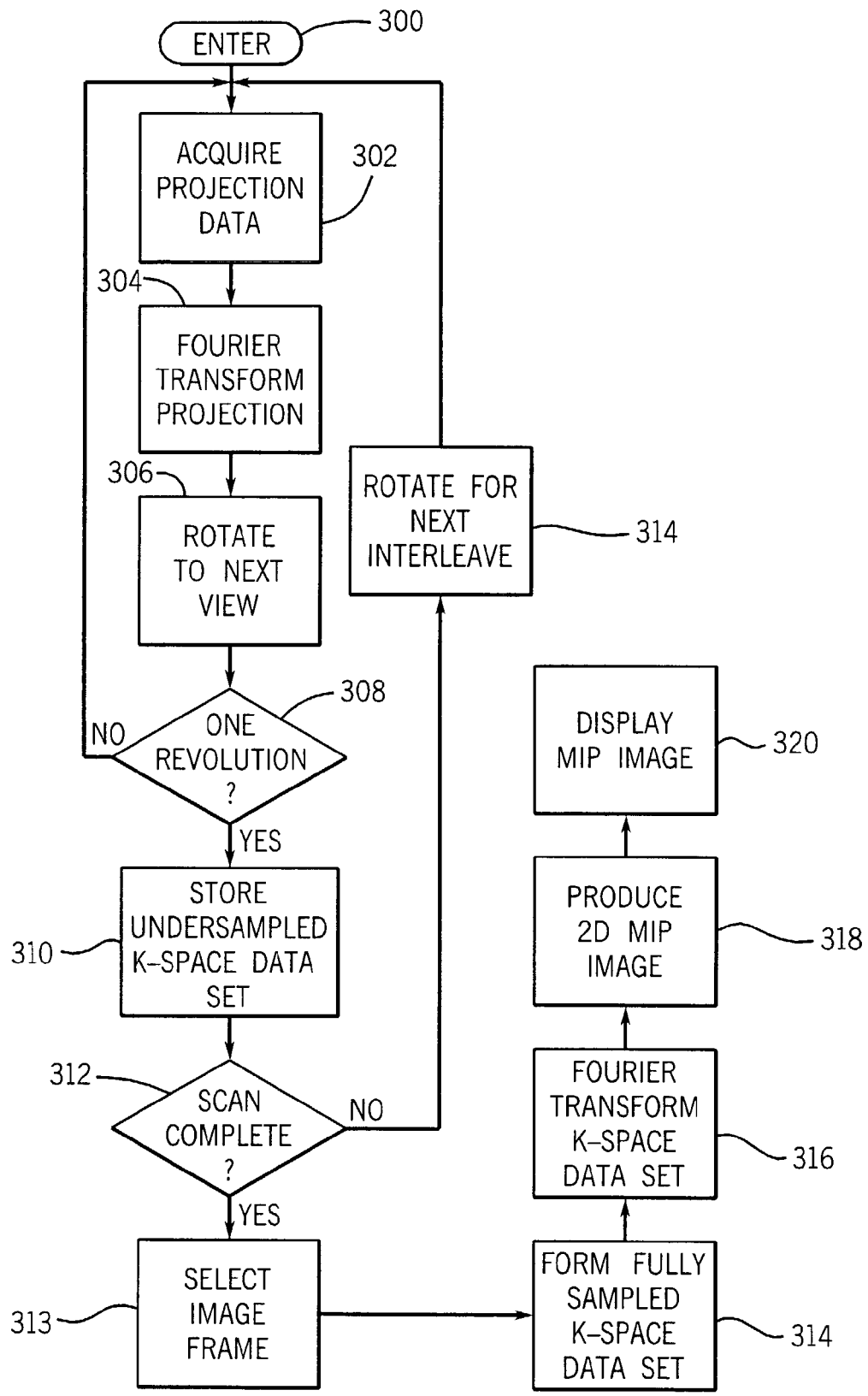
FIG. 7 is a flow chart of a preferred method for practicing the present invention.

The preferred embodiment of the procedure is shown in FIG. 7. A loop is entered at 300 in which a series of undersampled k-space data sets are acquired with a CT system during a dynamic study. As indicated at process block 302, one 2D array of projection data is acquired at a specific view angle and this data is Fourier transformed along the transverse, or row, direction at process block 304 to form a corresponding k-space projection at the same viewing angle. The CT system is then rotated to the next view angle as indicated at process block 306. This process continues until the x-ray source and detector have been rotated sufficiently around the subject to acquire data for an image as determined at decision block 308. Typically, this rotation is equal to 180° plus the beam fan angle.

As the gantry revolves one undersampled k-space data set is acquired and saved as indicated at process block 310. In the preferred embodiment this undersampled k-space data set contains one-third the number of views required for a fully sampled k-space data set (i.e. N/3). The system branches at decision block 312 and two more undersampled k-space data sets with view angles interleaved with the view angles of the first k-space data set are acquired. This is done by rotating the gantry by an amount equal to one-third the angle between acquired views as indicated at process block 314. For example, if 120 views are acquired for each undersampled k-space data set, the angle between successive views is 3°. The gantry is revolved 1° at process block 314 to acquire the second, interleaved set of k-space data and is revolved again 1° before acquiring the third interleaved set of k-space data.

The system remains in this loop during the entire dynamic study to acquire and store a series of undersampled k-space data sets. These data sets can be used to reconstruct images in near real time as the dynamic study is performed, but due to the undersampling, streak artifacts may be present. Nevertheless, these real-time images may be helpful in conducting the dynamic study.

The preferred dynamic study includes a pre-contrast phase during which at least three successive undersampled k-space data sets are acquired. These three pre-contrast data sets are combined to form a mask image which may be subtracted from the contrast-enhanced images. After the pre-contrast data sets are acquired the contrast agent is administered and successive undersampled k-space data sets are acquired and stored as the contrast enters the subject vasculature.

At the completion of the data acquisition phase of the dynamic study as determined at decision block 312, one or more image frames are selected for reconstruction as indicated at process block 313. This selection may be aided by reconstructing and displaying single undersampled k-space data sets in order to identify the optimal moment during the dynamic study in which peak contrast is present in the vasculature of interest. Preferably, three interleaved undersampled k-space data sets are selected at process block 323 and a fully sampled k-space data set is then formed as indicated at process block 314. As discussed above with respect to FIG. 6, this is done by combining all of the k-space data from the second of the three selected undersampled k-space data sets (m) with data from the peripheral k-space regions of the first and third undersampled k-space data sets (m−1 and m+1).

An image is then reconstructed from the resulting fully sampled k-space data set. As indicated at process block 316, the fully sampled k-space data set is first regridded to place the acquired data set on a 3D Cartesian grid. Such regridding methods are well known in the art and is described, for example, in J. Jackson et al, "Selection Of Convolution Function For Fourier Inversion Using Gridding," *IEEE Trans. Med. Imaging*, 10, 473–478, 1991. The resulting 3D array of k-space data are density compensated with a $\rho^2$ filter, where $\rho$ is the k-space radius of the data point being compensated. The $\rho=0$ point is weighted according to the finite sphere of volume that it samples, similar to the correction proposed for 2D projection filters. The kernel used for the regridding process is either a simple triangle function, which is computationally very fast, or a Kaiser-Bessel function, which has the advantage of reducing aliased energy from the regridding process. A 3D Fourier transformation is then performed on the regridded k-space data and a 3D magnitude image is produced from the transformed data.

A 2D maximum intensity pixel (MIP) image is then produced from the 3D magnitude image at process block 318 using a method such as that described by Sun Y, Parker D L, "Performance Analysis Of Maximum Intensity Projection Algorithm For Displaying Of MRA Images", *IEEE Trans. Med. Imaging*, 1999 December; 18(12):1154–69. The 3D magnitude image is typically displayed and the operator or physician manipulates the orientation of the image to select the optimal projection angle. The resulting 2D projection image may then be displayed on the console display as indicated at process block 320.

As discussed above, a better angiogram can be produced by subtracting a pre-contrast mask image from the contrast enhanced image. The mask image is produced by combining three successive pre-contrast undersampled k-space data sets as described above, regridding the fully sampled data set and then Fourier transforming the regridded 3D k-space data set. Preferably, the 3D mask image is subtracted from the 3D contrast enhanced image before producing the two-dimensional MIP image in step 318.

Rather than producing a single image at the selected optimal moment during the dynamic study, it is also possible to produce a series of images by sliding the window of three selected undersampled k-space data sets through the stored series of undersampled k-space data sets. A single mask image is reconstructed and subtracted from each resulting contrast enhanced image.

In some cases it may be desirable to form an image from a single, undersampled k-space data set. In order to best reduce the streak artifacts caused by bone, the pre-contrast mask image in this instance should be reconstructed from an undersampled k-space data set acquired at the same interleaved projection angles. This insures the best correspondence between the bone streaks in the selected post contrast image and the subtracted pre-injection mask image.

While it is preferable to produce the pre-injection mask image from a fully sampled k-space data set (i.e., acquired at all interleaved projection angles), some scan time can be saved by producing a mask image from one interleaved undersampled k-space data set. This single interleaved, undersampled mask image is thresholded to isolate the intense signals produced by bone. Less intense streak artifacts are thus removed to produce a model image of bone and other "bright" anatomy. This model image is reprojected at all the projection angles used in the final reconstructed post contrast image to form the mask image. This mask produces streak artifacts that register with those in the fully sampled post contrast image thus permitting their registered subtraction.

A third alternative is the removal of bone and other background signal using a segmentation method. For example, the reconstructed CT image time series may be analyzed to define the temporal contrast behavior of each voxel as the contrast agent arrives. Using regions of interest on the arteries, veins and background, the arteries can be segmented out without the need for a pre-injection mask. This technique is disclosed in U.S. Pat. No. 6,381,486, which is incorporated herein by reference.

A fourth alternative is the use of an MR UNFOLD technique to remove streaks. In this approach two sets of angular interleaves are obtained in successive time frames. The 1D Fourier transform places the streak signal at the acquisition Nyquist frequency where it can be removed by a temporal filter. This technique has been described by Madore B, Glover G H, Pelc N J, "Unaliasing By Fourier-Encoding The Overlaps Using The Temporal Dimension (UNFOLD) Applied To Cardiac Imaging And fMRI", *Magn. Reson. Med.* 1999 November; 42(5):813–28. In the present application, different amounts of temporal filtering would be used at different spatial frequencies.

A fifth alternative is the use of a matched filter to add the data acquired in successive undersampled frames. Here, SNR is increased through matched filtering or simple summation of time frames.

What is claimed is:

1. A method for producing an image with a computed tomography (CT) system, the steps comprising:
    a) positioning a subject in the CT system;
    b) acquiring a first undersampled image data set from a selected region of interest in the subject, the undersampled image data set comprising a plurality of projections acquired at a corresponding plurality of projection angles;
    c) transforming the undersampled image data set to form a corresponding first undersampled k-space data set;
    d) repeating steps b) and c) to produce a second undersampled k-space data set from a plurality of projections acquired at projection angles interleaved with the projection angles used to acquire the first undersampled image data set;
    e) combining k-space data from one of said undersampled k-space data sets with peripheral k-space data from the other undersampled k-space data set; and
    f) reconstructing an image of the region of interest by transforming the combined k-space data.

2. The method as recited in claim 1 in which the region of interest includes vasculature and the method further includes:
    g) injecting a contrast agent which flows into the vasculature;
    h) repeating steps b), c), d), e) and f) to produce a contrast enhanced image of the region of interest; and
    i) subtracting the image of the region of interest from the contrast enhanced image of the region of interest to produce an angiogram.

3. The method as recited in claim 2 in which steps h) and i) are repeated to produce a time series of angiograms that depict the vasculature as the contrast agent flows into the vasculature.

4. The method as recited in claim 1 which includes repeating steps b) and c) to produce a third undersampled k-space data set from a plurality of projections acquired at projection angles interleaved with the projection angles used to acquire the first and second undersampled image data sets; and
    step e) is performed by combining substantially all the k-space data from the second undersampled k-space data set with peripheral k-space data from the first and third undersampled k-space data sets.

5. The method as recited in claim 1 in which step c) is performed by Fourier transforming each acquired projection.

6. The method as recited in claim 1 in which step f) includes:
    regridding the combined k-space and;
    Fourier transforming the regridded k-space data.

7. A method for producing an image of a subject with a computed tomography x-ray imaging system, the steps comprising:
    a) acquiring a set of projection data with the imaging system from a selected view angle with respect to the subject;
    b) changing the view angle by a first selected amount;
    c) repeating steps a) and b) to acquire a first plurality of sets of projection data; d) transforming the first plurality of sets of projection data to form a first undersampled k-space data set;
    e) changing the view angle by a second selected amount which is less than said first selected amount;
    f) repeating steps a) and b) to acquire a second plurality of sets of projection data that are interleaved with the first plurality of sets of projection data;
    g) transforming the second plurality of sets of projection data to form a second undersampled k-space data set;
    h) combining the k-space data from one of said first or second undersampled k-space data sets with peripheral k-space data from the other of said first or second undersampled k-space data sets to form a more fully sampled k-space data set; and
    i) reconstructing an image from the more fully sampled k-space data set.

8. The method as recited in claim 7 in which the imaging system acquires x-ray attenuation projection data and the undersampled k-space data sets are formed in steps d) and g) by Fourier transforming each set of projection data in the respective first and second plurality of sets of projection data.

9. The method as recited in claim 8 in which each set of acquired projection data is a two-dimensional array of x-ray attenuation data and steps d) and g) are performed by Fourier transforming each set of projection data along one axis of the two-dimensional array of x-ray attenuation data.

10. The method as recited in claim 9 in which the undersampled k-space data sets and the more fully sampled k-space data sets are three-dimensional data sets and the reconstructed image is a three-dimensional image.

11. The method as recited in claim 10 which further includes:
   j) producing a two-dimensional projection image from the reconstructed three-dimensional image.

12. The method as recited in claim 7 in which step i) includes:
   regridding the more fully sampled k-space data set; and
   Fourier transforming the regridded k-space data set.

13. A method for producing an image of a subject with a computed tomography x-ray imaging system, the steps comprising:
   a) acquiring a series of undersampled image data sets with the imaging system, each successive undersampled image data set being a set of projections acquired at respective projection angles which are interleaved with projection angles used to acquire temporally adjacent undersampled image data sets;
   b) transforming the series of undersampled image data sets into a corresponding series of undersampled k-space data sets;
   c) selecting a plurality of the undersampled k-space data sets in said series;
   d) combining substantially all the k-space data from one of the selected undersampled k-space data set with peripheral k-space data from the other of the plurality of selected undersampled k-space data sets; and
   e) reconstructing an image from the combined k-space data.

14. The method as recited in claim 13 in which a time series of images are produced by repeating steps c), d) and e) a plurality of times and selecting a different plurality of undersampled k-space data sets in said series during each repetition.

15. The method as recited in claim 13 in which step a) is performed by acquiring the undersampled image data sets using three different sets of projection angles which are interleaved with each other.

16. The method as recited in claim 15 in which step c) is performed by selecting three successive undersampled k-space data sets in said series.

17. The method as recited in claim 16 in which step d) is performed by combining substantially all the k-space data from the second of the three selected successive undersampled k-space data sets with peripheral k-space data from the first and the third of the three selected successive undersampled k-space data sets.

18. The method as recited in claim 13 in which step b) is performed by Fourier transforming each projection.

19. The method as recited in claim 13 in which step d) includes:
   regridding the combined k-space data; and
   Fourier transforming the regridded k-space data.

20. The method as recited in claim 13 in which the imaging system acquires projections as a two-dimensional array of X-ray attenuation data and step b) is performed by Fourier transforming each projection along one axis of the two-dimensional array of x-ray attenuation data.

21. The method as recited in claim 13 in which a contrast agent is added to the subject during the performance of step a), and the undersampled k-space data sets selected in step c) are acquired after the addition of the contrast agent, the method further comprising:
   f) producing a mask image by repeating steps c), d) and e) with undersampled k-space data sets acquired before addition of the contrast agent; and
   g) subtracting the mask image from said image.

\* \* \* \* \*